(12) United States Patent
Silverman et al.

(10) Patent No.: US 8,158,605 B2
(45) Date of Patent: Apr. 17, 2012

(54) AZACYTIDINE ANALOGUES AND USES THEREOF

(75) Inventors: Lewis Silverman, Sleepy Hollow, NY (US); James Holland, Scarsdale, NY (US)

(73) Assignee: Mount Sinai School of Medicine, New York, NY (US)

( * ) Notice: Subject to any disclaimer, the term of this patent is extended or adjusted under 35 U.S.C. 154(b) by 186 days.

(21) Appl. No.: 12/238,125

(22) Filed: Sep. 25, 2008

(65) Prior Publication Data

US 2009/0209482 A1 Aug. 20, 2009

Related U.S. Application Data (60) Provisional application No. 60/975,437, filed on Sep. 26, 2007.

(51) Int. Cl.
*A01N 43/04* (2006.01)
*A61K 31/70* (2006.01)

(52) U.S. Cl. ............. 514/49; 514/43; 514/50; 536/28.1; 536/28.3

(58) Field of Classification Search .................. None
See application file for complete search history.

(56) References Cited

U.S. PATENT DOCUMENTS

| | | | |
|---|---|---|---|
| 3,171,833 A | 3/1965 | Sorm et al. |
| 3,350,388 A | 10/1967 | Sorm et al. |
| 3,817,980 A | 6/1974 | Vorbruggen et al. |
| 3,891,623 A | 6/1975 | Vorbruggen et al. |
| 3,984,396 A | 10/1976 | Witkowski et al. |
| 3,998,807 A | 12/1976 | Moffatt |
| 4,172,889 A | 10/1979 | Wechter et al. |
| 4,405,611 A | 9/1983 | Chatterji et al. |
| 4,981,613 A | 1/1991 | Okazaki et al. |
| 5,223,263 A | 6/1993 | Hostetler et al. |
| 5,385,912 A | 1/1995 | Neuenschwander et al. |
| 5,480,883 A | 1/1996 | Spada et al. |
| 5,919,815 A | 7/1999 | Bradley et al. |
| 5,994,354 A | 11/1999 | Pelosi, Jr. et al. |
| 6,080,877 A | 6/2000 | Swindell et al. |
| 6,153,594 A | 11/2000 | Borretzen et al. |
| 6,258,584 B1 | 7/2001 | Prockop et al. |
| 6,258,811 B1 | 7/2001 | Yamauchi et al. |
| 6,316,425 B1 | 11/2001 | Myhren et al. |
| 6,335,322 B1 | 1/2002 | Myhren et al. |
| 6,358,960 B1 | 3/2002 | Senokuchi et al. |
| 6,372,725 B1 | 4/2002 | Zileh et al. |
| 6,384,019 B1 | 5/2002 | Myhren et al. |
| 6,407,094 B1 | 6/2002 | Adam et al. |
| 6,407,137 B2 | 6/2002 | Shashoua |
| 6,548,486 B1 | 4/2003 | Dalen et al. |
| 6,576,636 B2 | 6/2003 | Webb et al. |
| 6,670,341 B1 | 12/2003 | Kucera et al. |
| 6,762,175 B2 | 7/2004 | Myhren et al. |
| 6,887,855 B2 | 5/2005 | Ionescu et al. |
| 6,943,249 B2 | 9/2005 | Ionescu et al. |
| 6,998,391 B2 | 2/2006 | Lyons et al. |
| 2001/0006962 A1 | 7/2001 | Myhren et al. |
| 2002/0042391 A1 | 4/2002 | Myhren et al. |
| 2003/0153544 A1 | 8/2003 | Myhren et al. |
| 2004/0063677 A1 | 4/2004 | Myhren et al. |
| 2004/0127436 A1 | 7/2004 | Daifuku et al. |
| 2004/0180949 A1 | 9/2004 | Shashoua et al. |
| 2004/0186283 A1 | 9/2004 | Ionescu et al. |
| 2005/0014752 A1 | 1/2005 | Daifuku et al. |
| 2005/0227367 A1 | 10/2005 | Luna et al. |
| 2006/0063735 A1 | 3/2006 | Redkar et al. |
| 2006/0205685 A1 | 9/2006 | Phiasivongsa et al. |
| 2006/0205687 A1 | 9/2006 | Phiasivongsa et al. |
| 2007/0135436 A1 | 6/2007 | Myhren et al. |
| 2007/0225248 A1 | 9/2007 | Myhren et al. |
| 2009/0209477 A1 | 8/2009 | Silverman et al. |

FOREIGN PATENT DOCUMENTS

| | | |
|---|---|---|
| CA | 2468099 A1 | 5/2003 |
| CS | 264454 B1 | 8/1989 |
| CS | 264456 B1 | 8/1989 |

(Continued)

OTHER PUBLICATIONS

Kroger et al. General Pharmacology (1999), vol. 33, pp. 195-201.*

(Continued)

*Primary Examiner* — Patrick Lewis
(74) *Attorney, Agent, or Firm* — LeClairRyan, a Professional Corporation (57) ABSTRACT

The present invention is directed toward compounds of Formula (I) as follows:

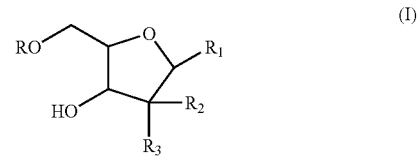

(I)

wherein,
R is H, $R_5C(O)$;
$R_1$ is

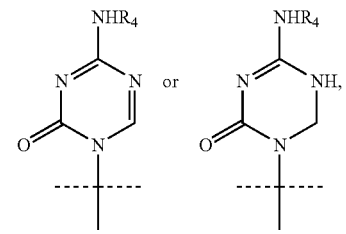

where the crossing dashed line illustrates the bond formed joining $R_1$ to the molecule of Formula (I);
$R_2$ and $R_3$ are independently OH or H, provided that $R_2$ and $R_3$ are not simultaneously OH;
$R_4$ is H or $R_5C(O)$, provided that R and $R_4$ are not simultaneously H; and
$R_5$ is a $C_3$-$C_{26}$ alkenyl,
or a pharmaceutical salt thereof.
Methods of making and using these compounds are also disclosed.

9 Claims, 7 Drawing Sheets

FOREIGN PATENT DOCUMENTS

| | | |
|---|---|---|
| EP | 0056265 A2 | 7/1982 |
| EP | 0393920 B1 | 10/1990 |
| EP | 0 515 156 B1 | 11/1992 |
| EP | 0545966 B1 | 11/1994 |
| EP | 0977725 B1 | 6/2004 |
| WO | 97/05143 A1 | 2/1997 |
| WO | 97/05154 A1 | 2/1997 |
| WO | 97/09878 A1 | 3/1997 |
| WO | 99/26958 A1 | 6/1999 |
| WO | 00/76979 A1 | 12/2000 |
| WO | 01/18013 A1 | 3/2001 |
| WO | 2004/028454 A2 | 4/2004 |
| WO | 2004/101593 A1 | 11/2004 |
| WO | 2004/112716 A2 | 12/2004 |
| WO | 2005/044797 A1 | 5/2005 |
| WO | 2005/065150 A2 | 7/2005 |
| WO | 2005/066162 A1 | 7/2005 |
| WO | 2005/075482 A1 | 8/2005 |
| WO | 2005/115410 A3 | 12/2005 |
| WO | 2006/024858 A1 | 3/2006 |
| WO | 2006/034154 A3 | 3/2006 |
| WO | 2006/048771 A1 | 5/2006 |
| WO | 2006/063111 A2 | 6/2006 |
| WO | 2006/099132 A1 | 9/2006 |
| WO | 2007/035783 A2 | 3/2007 |
| WO | 2007/037187 A1 | 4/2007 |
| WO | 2007/067071 A1 | 6/2007 |
| WO | 2009/042767 A1 | 4/2009 |

OTHER PUBLICATIONS

Karon et al. Blood (1973), vol. 42, pp. 359-365.*

Andrei, G. et al., Antiviral Research, 45:157-167 (2000). "Antiviral activity of ganciclovir elaidic acid ester against herpes viruses."

Balzarini, J. et al., Gene Therapy, 5:419-426 (1998). "Superior cytostatic activity of the ganciclovir elaidic acid ester due to the prolonged intracellular retention of ganciclovir anabolites in herpes simplex virus type 1 thymidine kinase gene-transfected tumor cells."

Bergman, A.M. et al., Biochemical Pharmacology, 67:503-511 (2004). "Antiproliferative activity and mechanism of action of fatty acid derivatives of arabinofuranosylcytosine in leukemia and solid tumor cell lines."

Breistol, K. et al., Cancer Research, 59:2944-2949 (1999). "Antitumor Activity of P-4055 (Elaidic Acid-Cytarabine) Compared to Cytarabine in Metastatic and s.c. Human Tumor Xenograft Models."

Jennings, R. et al., Antimicrobial Agents and Chemotherapy, 43(1):53-61 (1999). "Evaluation of a Novel, Anti-Herpes Simplex Virus Compound, Acyclovir Elaidate (P-4010), in the Female Guinea Pig Model of Genital Herpes."

Pouton, C.W., European Journal of Pharmaceutical Sciences, 11 (Suppl. 2):S93-S98 (2000). "Lipid formulations for oral administration of drugs: non-emulsifying, self-emulsifying and 'self-microemulsifying' drug delivery systems."

International Search Report for International Patent Application No. PCT/US08/77669 (Dec. 2, 2008).

International Search Report and Written Opinion for PCT/US08/77673 (Dec. 2, 2008).

Final Office Action, U.S. Appl. No. 12/238,054 (May 17, 2011).

International Search Report and Written Opinion for PCT/US2008/077669 dated Dec. 2, 2008.

* cited by examiner

AZACYTIDINE ANALOGUES AND USES THEREOF

This application claims benefit of U.S. Provisional Patent Application Ser. No. 60/975,437, filed Sep. 26, 2007, which is hereby incorporated by reference in its entirety.

FIELD OF THE INVENTION

This invention relates to azacytidine analogues and uses thereof.

BACKGROUND OF THE INVENTION

Nucleoside analogues, the derivatives of the natural nucleosides found as building blocks of DNA and RNA, are effective in the clinical treatment of human cancer or viral diseases, although in the early years such compounds were evaluated as anti-tuberculosis agents. Such compounds have been registered in the market for more than 40 years, and approximately 35 products are currently in daily use. The natural nucleosides illustrated in Table 1 below, are constructed from two classes of nitrogen bases, i.e. the purines (exemplified by adenine and guanine) and the pyrimidines (exemplified by thymine, uracil, and cytosine) and from the monosaccharide ribose or deoxyribose.

TABLE 1

The natural nucleosides all exist in the so called β-D configuration as illustrated in the Formula A below. The nitrogen base and the hydroxy-methyl side chain on the sugar ring are both on the same side (cis) of the plane of the sugar ring.

Formula A

In order to obtain nucleoside derivatives with anticancer or antiviral activity, chemical modifications in either the nitrogen base and/or the monosaccharide have been performed. For instance in the nitrogen base, the addition of halogen atoms or other functional groups, insertion of additional nitrogen atoms or a stereochemical change in the monosaccharide ring from ribose to arabinose or removal of the hydroxyl group to deoxyribose may lead to products with a potential therapeutic benefit. In many products, the monosaccharide ring is conserved, while in others, the sugar ring has been changed into a chain. The nucleoside analogues are small molecules with fair to excellent aqueous solubility.

The extensive research and development effort put into the area of nucleoside analogues due to the worldwide AIDS epidemic bolstered the basic knowledge and understanding of mechanism of action, alterations in activity profile due to chemical modifications etc, are also relevant to the field of cancer treatment.

A general weakness with many drugs, including nucleoside analogues, is low activity and inferior specificity for treatment of the actual disease in question. Some of these problems may be related to the inherent activity of the drug substance itself, some may be related to certain resistance mechanisms (either inherent in the patient or acquired during treatment e.g. multiple drug resistance (MDR) in cancer treatment). Some problems may be related to certain inferior transport or cellular uptake and activation mechanisms. Some problems may be related to rapid inactivation and/or excretion of the drug.

The efficacy of nucleoside analogues depends on a large extent on their ability to mimic natural nucleosides, thus interacting with viral and/or cellular enzymes and interfering with or inhibiting critical processes in the metabolism of nucleic acids. In order to exert their antiviral or anti-cancer activity, the nucleoside analogues have to be transformed, via their mono- and di-phosphates, into their corresponding tri-phosphates through the action of viral and/or cellular kinases. As a general rule, the tri-phosphate is the active agent, but for some products, e.g. gemcitabine, even the di-phosphate may exert a clinically significant effect.

In order to reach the diseased, cancerous or virus infected cells or tissues, following either enteral or parenteral administration, the nucleoside analogues should have favorable pharmacokinetic characteristics. In addition to rapid excretion of the administered drug, many nucleoside analogues may be deactivated both in the blood stream and in tissues. For instance may cytosine derivatives, even at the monophosphate level, be rapidly deaminated through the action of a class of enzymes called deaminases, to the inactive uracil analogue. The cellular uptake and thus good therapeutic efficacy of many nucleoside analogues strongly depend on membrane bound nucleoside transport proteins (called concentrative and equilibrative nucleoside transporters). Hence, compounds that do not rely on such specific uptake mechanisms are sought. Yet another activity limiting factor, particularly within the anti-cancer field, are the cellular repair mechanisms. When an anti-cancer nucleoside analogue mono-phosphate is incorporated into the cellular DNA, it should not be removed from the cancer cell DNA due to the exonuclease activity linked to the p53 protein. However, removal of a nucleoside analogue from the DNA of a healthy cell is favorable in order to limit the side effects of the drug.

Over the years, many nucleoside analogues have been developed that to a large extent overcome some or many of the activity limiting features. As an example, acyclovir (ACV) can be given to illustrate a compound with great specificity. The ACV-mono-phosphate can only be formed by viral kinases meaning that ACV cannot be activated in uninfected cells. Despite this fact, ACV is not a particularly active product. In order to circumvent the often rate limiting step in the activation of a nucleoside analogue, the intracellular formation of the nucleoside analogue mono-phosphate, several phosphonates, such as cidofovir or even mono-phosphate products, have been developed. In order to facilitate oral uptake or to secure a favorable drug disposition in the body, particular prodrugs such as Hepsera have been made.

In addition to the structural changes made to nucleoside analogues to facilitate enhanced clinical utility, further modifications have been made to improve the activity. There are several examples of modified nucleoside analogues resulting from the addition of lipid moieties (U.S. Pat. Nos. 6,153,594, 6,548,486, 6,316,425, and 6,384,019; European Patent Application Nos. EP-A-56265 and EP-A-393920; and WO 99/26958). This can be achieved by the linking of fatty acids through, for instance, an ester, amide, carbonate, or carbamate bond. More elaborate products can be made, such as phospholipid derivatives of the nucleoside analogues. See *Eur J Pharm Sci* 11b Suppl 2: 15-27 (2000); European Patent No. 545966; Canadian Patent No. 2468099; and U.S. Pat. Nos. 6,372,725 and 6,670,341. Such analogues are described to have antiviral activity that is particularly suitable for the therapy and prophylaxis of infections caused by DNA, RNA, or retroviruses. They are also suited for treatment of malignant tumours. The nucleoside analogue lipid derivatives may serve several purposes. They may be regarded as a prodrug that is not a substrate for deaminases, thereby protecting the nucleoside analogues from deactivation during transport in the bloodstream. The lipid derivatives may also be more efficiently transported across the cellular membrane, resulting in enhanced intracellular concentration of the nucleoside analogue. Lipid derivatives may also be more suited for use in dermal preparations, oral products (see U.S. Pat. No. 6,576, 636 and WO 01/18013), or particular formulations such as liposomes (see U.S. Pat. No. 5,223,263) designed for tumor targeting.

It has been demonstrated that for nucleoside analogues with a conserved β-D configuration of the monosaccharide ring, or for nucleoside analogues with a non-cyclic side chain, the antiviral or anticancer activity can be most efficiently improved through the formation of lipid derivatives of mono-unsaturated ω-9 C18 and C20 fatty acids. See *Antimicrobial Agents and Chemotherapy*, Vol., 53-61 (1999); *Cancer Research* 59: 2944-2949 (1999); *Gene Therapy*, 5: 419-426 (1998); Antiviral Research, 45: 157-167 (2000); and *Biochemical Pharmacology*, 67: 503-511 (2004). The preferred mono-unsaturated derivatives are not only more active than the poly-unsaturated counterparts but are more crystalline and chemically stable towards oxidation of the lipid chain. Hence, they are more favorable compounds from a chemical and pharmaceutical manufacturing point of view. It has also been demonstrated that the mono-unsaturated ω-9 C18 and C20 fatty acids are suited for improvement of the therapeutic activity of a large number of non-nucleoside biologically active compounds (see European Patent No. 0977725).

A relatively new subgroup of nucleoside analogues are the so called aza-C derivatives. In this class of compounds, the CH group in the 5 position in the pyrimidine base is exchanged with a nitrogen atom as shown in Formula B below.

Formula B

Tumor suppressor genes that have been silenced by aberrant DNA methylation are potential targets for reactivation by these novel chemotherapeutic agents. The potent inhibitors of DNA methylation and antileukemic agents, aza-cytidine and 5-aza-2'-deoxycytidine derivatives (5-aza-C, 5-aza-CdR, Decitabine), can reactivate silent tumor suppressor genes. At high concentrations, the compounds are cytotoxic, but at lower concentrations the hypomethylation leads to differentiation of cell lines. The compounds require metabolic activation by deoxycytidine kinase, and produces an inhibition of DNA methyltransferase. One hindrance to the curative potential of these derivatives are their rapid in vivo inactivation by cytidine deaminase (CD). The instability in aqueous solutions as well as their side effect profiles have limited their clinical activity.

The present invention is directed to overcoming these and other deficiencies in the art.

SUMMARY OF THE INVENTION

One aspect of the present invention is directed toward a compound according to Formula (I)

wherein R is H, $R_5C(O)$; $R_1$ is where the crossing dashed line illustrates the bond formed joining $R_1$ to the molecule of Formula (I), $R_2$ and $R_3$ are independently OH or H, provided that $R_2$ and $R_3$ are not simultaneously OH, $R_4$ is H or $R_5C(O)$, provided that R and $R_4$ are not simultaneously H, $R_5$ is a $C_3$-$C_{26}$ alkenyl, or a pharmaceutical salt thereof.

Another aspect of the present invention is directed toward a pharmaceutical composition comprising the compound of Formula (I) and a pharmaceutical excipient, diluent, and/or carrier.

A further aspect of the present invention is directed toward a method of treating a subject for a neoplastic condition. The method includes selecting a subject with a neoplastic condition and administering to the subject a compound of Formula (I), as described above, or a pharmaceutical salt thereof, under conditions effective to treat the neoplastic condition in the subject.

A further aspect of the present invention is directed toward a method of treating a subject for an inflammatory condition. The method includes selecting a subject with an inflammatory condition and administering to the subject a compound of Formula (I), as described above, or a pharmaceutical salt thereof, under conditions effective to treat the inflammatory condition in the subject.

The instability of Aza-C in buffer and plasma is well known (see Israili et al., Cancer Research 36, 1453-1461 (1976); Rudek et al., J Clin Oncol, 23:17, 3906-3911 (2005); Rustum et al., J Chromat, 421:12, 387-91 (1987); Zhao et al., J Chromat B, 813, 81-88 (2004), which are hereby incorporated by reference in their entirety). An average terminal half-life of 1.50±2.30 hours in clinical plasma samples has been reported for Aza-C (see Rudek et al., J Clin Oncol, 23:17, 3906-3911 (2005), which is hereby incorporated by reference in its entirety). In vitro, a 20% loss of Aza-C even at −60° C. is noted after 4.5 days storage and a 10% loss within 0.5 hours when stored at room temperature (see Zhao et al., J Chromat B, 813, 81-88 (2004), which is hereby incorporated by reference in its entirety). The prime instability of Aza-C is thought to be due to a rapid (first step being reversible) ring opening of the 5-Aza-pyrimidine ring with a subsequent elimination of formic acid (see Chan et al., J Pharma Sci, 68; 7, 807-12 (1979), which is hereby incorporated by reference in its entirety). Other degradation pathways are thought to be deamination of the position 4 amino group and hydrolysis of the glycoside bond to give D-ribose and 5-azacytosine. It has been surprisingly found that the preferred Aza-C lipid derivatives have a significantly better plasma stability profile than Aza-C itself. The compounds are stable (percent remaining of initial ≧94%) in blank human plasma matrix at room temperature for at least 4 hours under the experimental conditions, and no significant degradation products were observed in the post-extract supernatant after precipitation of plasma proteins. The plasma stability of the preferred lipid compounds have been examined further when stored at 37° C. It is shown that the ring-opening of the Aza-moiety or other degradation of the compound is significantly reduced when the lipid side chain is attached to Aza-C.

The rapid degradation of Aza-C is a drawback for clinical use of Aza-C. The enhanced plasma stability of the lipid derivatives over Aza-C itself may give both a high and sustained patient plasma level of the lipid derivative. This may lead to a better tissue/organ/tumor distribution and cellular exposure to and uptake of the drug than for Aza-C itself in the first hand, and subsequently better tumor cell DNA exposure to Aza-C after intracellular hydrolysis of the Aza-C-5'-ester bond.

Embodiments of the present invention create, through the modification of azacytidine and deoxycytidine (e.g., 5-aza-2'-deoxycytidine), novel molecules with surprisingly different properties compared to azacytidine and deoxycytidine (e.g., 5-aza-2'-deoxycytidine). This creates a series of compounds with activity that extends well beyond the anti-cancer activity of azacytidine and deoxycytidine (e.g., 5-aza-2'-deoxycytidine) which is limited to hematologic malignancies. These novel compounds have anti-cancer efficacy against a broad array of solid tumors including breast and cervical cancer. The compounds are also surprisingly active against cancers which are resistant to treatment and thus can offer a therapeutic advantage in solid tumors where current treatment choices are limited. Embodiments of the present invention have therapeutic uses to treat cancers where options and efficacy remain limited and fulfill an unmet need.

These compounds exhibit an earlier onset of activity after limited exposure and, therefore, can be effective after only a short duration of treatment in the clinical setting. This would translate into shorter, less frequent treatment exposure and a reduction in drug-related toxicities compared to the parent drugs. This would provide for an enhanced therapeutic index.

The alteration in the structure with the addition of the lipid (includes both esters and amides) component conserves the azole cytidine ring and thus the effects of the molecule on epigenetic mechanisms. Epigenetic modulation offers an important mechanism for altering gene expression in cancer and inflammation. These novel compounds have activity at lower concentrations than azacytidine and, thus, are more potent. These compounds with an altered spectrum of activity can modulate epigenetic targets in solid tumors and inflammatory diseases.

Epigenetic mechanisms are important in pro-inflammatory states which include, but are not exclusive to, inflammatory states of the lung, connective tissues, gastro-intestinal tract and vasculature. These compounds by targeting epigenetic mechanisms can reduce or reverse the inflammatory processes responsible for these diseases.

BRIEF DESCRIPTION OF THE DRAWINGS

In FIG. 2A, HL60, K562, and U937 cells were untreated or treated with 5-azacytidine 5'-elaidate (CP) (0.5-4 µM) for 24 hours. The percentage of apoptotic cells was determined with the aid of a fluoresence microscope after staining with acridine orange and ethidium bromide. In FIG. 2B, both HL60 and K562 were untreated or treated with 5-azacytidine 5'-elaidate (1, 2, or 4 µM) for 24 hours. The percentage of apoptotic cells was determined by flow cytometry using Annexin-V and PI staining.

DETAILED DESCRIPTION OF THE INVENTION

One aspect of the present invention is directed toward a compound according to Formula (I)

(I)

wherein R is H, $R_5C(O)$; $R_1$ is where the crossing dashed line illustrates the bond formed joining $R_1$ to the molecule of Formula (I), $R_2$ and $R_3$ are independently OH or H, provided that $R_2$ and $R_3$ are not simultaneously OH, $R_4$ is H or $R_5C(O)$, provided that R and $R_4$ are not simultaneously H, $R_5$ is a $C_3$-$C_{26}$ alkenyl, or a pharmaceutical salt thereof.

In certain embodiments, $R_5$ may be a $C_9$-$C_{26}$ alkenyl.

In a preferred embodiment, R is $R_5C(O)$, $R_1$ is $R_2$ is H, $R_3$ is OH, $R_4$ is H, and $R_5$ is $CH_3$—$(CH_2)_7$—CH=CH—$(CH_2)_7$—.

A broader aspect of the present invention is directed toward a compound according to Formula (I)'

(I)' wherein R is H, $R_5C(O)$, $R_5CH_2OC(O)$, or $R_5CH_2NHC(O)$, $R_1$ is where the crossing dashed line illustrates the bond formed joining $R_1$ to the molecule of Formula (I)', $R_2$ and $R_3$ are independently OH or H, provided that $R_2$ and $R_3$ are not simultaneously OH, $R_4$ is H, $R_5C(O)$, $R_5CH_2OC(O)$, or $R_5CH_2NHC(O)$, provided that R and $R_4$ are not simultaneously H, and $R_5$ is a $C_3$-$C_{26}$ alkenyl, or a pharmaceutical salt thereof.

In a preferred embodiment of the compound according to Formula (I)', k is 7 and n is 7. In certain embodiments, $R_1$ is where the crossing dashed line illustrates the bond formed joining $R_1$ to the molecule of Formula (I)'. In some embodiments, $R_4$ may be H. In certain embodiments, R is $R_5C(O)$, k is 7, m is 0, n is 7, $R_2$ is H, and $R_3$ is OH. In certain embodiments $R_5$ is a $C_9$-$C_{26}$ alkenyl.

Another aspect of the present invention is directed toward a pharmaceutical composition comprising the compound of Formula (I) and a pharmaceutical excipient, diluent, and/or carrier.

Agents of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active agents of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active agents may be incorporated with excipients and used in the form of tablets, capsules, elixirs, suspensions, syrups, and the like. Such compositions and preparations should contain at least 0.1% of active agent. The percentage of the agent in these compositions may, of course, be varied and may conveniently be between about 2% to about 60% of the weight of the unit. The amount of active agent in such therapeutically useful compositions is such that a suitable dosage will be obtained. Preferred compositions according to the present invention are prepared so that an oral dosage unit contains between about 1 and 250 mg of active agent.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to the active ingredient, sucrose as a sweetening agent, methyl and propylparabens as preservatives, a dye, and flavoring such as cherry or orange flavor.

These active agents may also be administered parenterally. Solutions or suspensions of these active agents can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents of the present invention may also be administered directly to the airways in the form of an aerosol. For use as aerosols, the agents of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

A further aspect of the present invention is directed toward a method of treating a subject for a neoplastic condition. The method includes selecting a subject with a neoplastic condition and administering to the subject a compound of Formula (I), as described above, or a pharmaceutical salt thereof, under conditions effective to treat the neoplastic condition in the subject.

In certain embodiments, the neoplastic condition is a cancerous disease. The cancerous disease may be a solid tumor or a hematological cancer or malignancy. The cancerous disease may be leukemia, lymphoma, multiple myeloma, or myelodysplastic syndrome.

In certain embodiments, the solid tumor may be a cancer of a tissue such as breast, ovary, prostate, brain, bladder, and lung tissues.

A further aspect of the present invention is directed toward a method of treating a subject for an inflammatory condition. The method includes selecting a subject with a an inflammatory condition and administering to the subject a compound of Formula (I), as described above, or a pharmaceutical salt thereof, under conditions effective to treat the inflammatory condition in the subject.

In certain embodiments the inflammatory condition is an inflammatory state of the lung, connective tissue, gastrointestinal tract, or vasculature.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

EXAMPLES

Example 1

Reagents, Cell Lines, and Cell Culture 5-azacytidine 5'-elaidate (CP or CP-4200) was obtained from Clavis Pharma AS Company, cell proliferation reagent WST-1 was obtained from Roche Applied Science (Manheim, Germany), PI and Annexin V-FITC apoptosis kit were purchased from BD Biosciences, Palo Alto, Calif., 5-azacytidine (5-AzaC), ethidium bromide (EB), acridine orange (AO), nitro blue tetrazolium (NBT), phorbol 12-myristate 13-acetate (TPA) were purchased from Sigma Chemical Co (St. Louis, Mo.).

Human promyelocytic leukemia cell lines HL60, human histiocytic lymphoma U937, human chronic myelogenous leukemia K562, human acute T cell Jurkat, breast adenocarcinoma MCF-7, urinary bladder carcinoma 5637, prostate carcinoma DU-145 were purchased from American Type Culture Collection. All cell lines except Jurkat were maintained in RPMI 1640 medium (Gibco, Glasgow, UK) supplemented with 10% heat-inactivated fetal calf serum (FCS), 100 U/ml of penicillin, and 100 mg/ml streptomycin, in an atmosphere of 5% $CO_2$ at 37° C. Jurkat cells were cultured in RPMI 1640 medium supplemented with 1.5 g/L sodium bicarbonate, 4.5 g/L glucose, 10 mM sodium pyruvate, and 10% FCS, 100 U/ml of penicillin, and 100 mg/ml streptomycin.

Example 2

Cytotoxicity Assay

The cytotoxicity of 5-azacytidine lipid was determined by calorimetric assay based on the cleavage of the tetrazolium salt WST-1 (4-[3-(4-Iodophenyl)-2-(4-nitrophenyl)-2H-5-tetrazolio]-1,3-benzene disulfonate) by mitochondrial dehydrogenases in viable cells. Cells were seeded at an initial concentration of $1\times10^6$/ml (HL60 cells) or $1.25\times10^5$/ml (U937, K562 and Jurkat) in medium with or without various concentrations of 5-azacytidine lipid in a 96-well flat bottom micro-plates and cultured for 24 to 72 hours. MCF-7, DU-145, and 5637 cells ($1\times10^4$/ml) were plated and allowed to adhere and spread for 24 hours. The various concentrations of 5-azacytidine lipid were added and cultures were maintained for an additional 24 to 72 hours. Cultures were incubated with WST-1 reagent for 1 hour. The production of formazan was measured by a microplate reader (Bio-Tek Instruments, Elx 800) at 450 nm with a reference wavelength of 650 nm. Growth inhibition was determined as compared to untreated cells (%). $IC_{50}$ values were calculated using CalcuSyn software (Biosoft).

Example 3

Quantitation of Apoptotic Cells

Apoptotic cells were defined using morphological criteria and fluorescence-activated cell sorting (FACS) after staining with Annexin V-FITC. For morphologic analysis, 1 μl of stock solution containing 100 μg/ml AO and 100 μg/ml EB was added to 25 μl cells suspension. The apoptitic cells and apoptotic bodies were analyzed with the aid of a fluorescence microscopy. The percentage of apoptotic cells was calculated after counting total 300 cells. For FACS analysis, 2×105 to 5×106 cells were washed with PBS and then labeled with Annexin V-FICS and propidium iodide (PI) in medium-binding reagent according to the Annexin V-FITC apoptosis detection kit instruction provided by the manufacturer. Fluorescent signals of FITC and PI were detected, respectively, at 518 nm and at 620 nm on FACSCAN (Becton Dickinson, San Jose, Calif.). The log of Annexin V-FITC fluorescence was displayed on the X-axis and the log of PI fluorescence was displayed on the Y axis. The data was analyzed by the CellQuest program (Becton Dickinson). For each analysis, 10,000 cells events were recorded.

Example 4

Cell Cycle

Cells were pelleted by centrifugation, and washed twice with PBS, fixed with 70% (v/v) cold ethanol (−20° C.), and stored at 4° C. for at least 24 hours. The cells were washed in PBS. Cell pellets were stained with PI/RNase staining solution. The cell suspension was incubated in the dark at room temperature for 30 min. DNA content was determined using a FACSCalibur flow cytometry (Becton Dickinson, Mount View, Calif.). Percentages of cells in Sub-G1, $G_1$, S and $G_2$/M stages of the cell cycle were determined with DNA histogram-fitting program (Becton Dickinson). A minimum of 10,000 events per sample was recorded.

Example 5

Synthesis of Aza-C-5'-oleic Acid Ester

Oleic acid (1.77 mmol, 500 mg) was dissolved in toluene (3 ml). DMF (10 μl) was added, followed by oxalyl chloride (3.6 mmol, 457 mg) over 10 min at room temperature. After 3 h, the toluene was removed in vacuo.

Aza-C (1.75 mmol, 427 mg) was suspended in DMA (6 ml), HCl (1 M in $Et_2O$, 2.0 mmol, 2.0 ml) was added, and, after 5 min at room temperature, the $Et_2O$ was removed in vacuo. The resulting turbid solution was cooled in an ice-water bath, and the acid chloride, dissolved in DMA (2 ml), was added over 2 h. The reaction mixture was stirred overnight while the temperature slowly reached room temperature, then it was heated at 30 C for 2 h. After cooling to room temperature, the reaction mixture was partitioned between saturated. aq. $NaHCO_3$, and EtOAc (25 ml of each). The aqueous phase was extracted with another 3×25 ml EtOAc. The organic phases were combined, washed with brine, and dried ($MgSO_4$). After removal of the solvents in vacuo, the crude, oily product was purified by flash chromatography ($SiO_2$, $CH_2Cl_2$ with 2.5, 5, and 10% MeOH). Yield: 110 mg (13%).

Example 6

Synthesis of 5-azacytidine 5'-elaidic Acid Ester 5-azacytidine (4.1 mmol, 1.00 g) was suspended in dry DMA (15 ml), and a solution of HCl in diethyl ether (4.9 mmol, 1 M, 4.9 ml) was slowly added at room temperature to give a clear solution. The ether was then removed in vacuo, resulting in a slightly turbid solution. A solution of elaidoyl chloride (4.8 mmol, 1.44 g) in dry DMA (8 ml) was added over 1 h at room temperature. The reaction mixture was then heated at 30° C. overnight, cooled to room temperature, and quenched with methanol (0.05 ml). After at least 1 h, the reaction mixture was concentrated at ca. $10^{-2}$ mbar and the residue was partitioned between saturated aq. $NaHCO_3$ and ethyl acetate. The aqueous phase was extracted with ethyl acetate. The organic phases where then combined, washed (brine), dried ($Na_2SO_4$), and concentrated in vacuo. Purification by flash chromatography ($SiO_2$, $CH_2Cl_2$ with 0-10% methanol) gave 0.9 g (43%) product.

Example 7

In Vitro Effect of 5-azacytidine 5'-elaidate on Tumor Cells

Figure 1A:
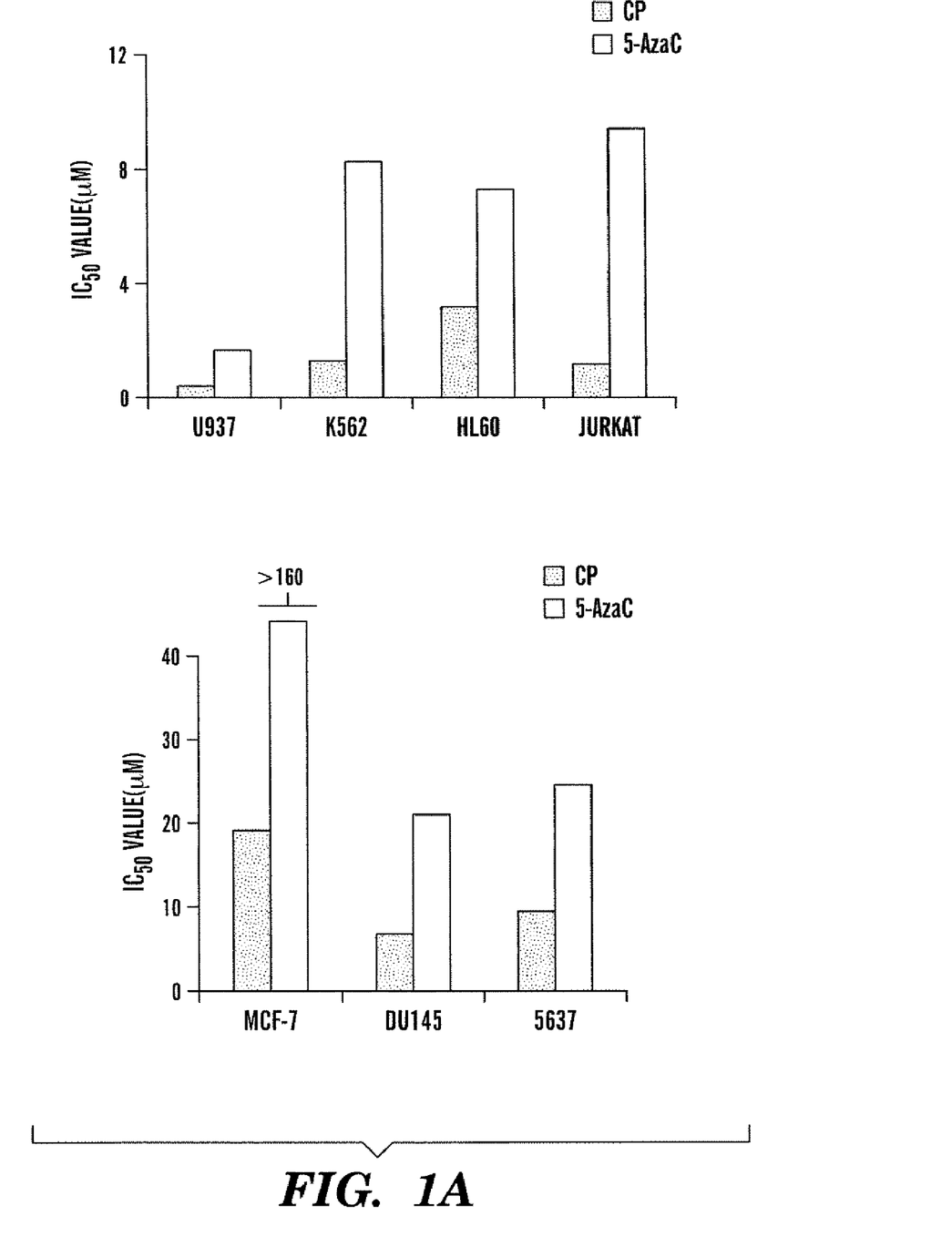
FIGS. 1A-B show graphs of comparative cytotoxic activity of 5-azacytidine 5'-elaidate (CP) and 5-AzaC on leukemia and solid tumor cell lines. Cytotoxicity was determined in the WST-1 assay. IC50 were calculated using CalcySyn software. The cells were treated for 24 hour (FIG. 1A) or the cells were treated for 24, 48, and 72 hour (FIG. 1B).
Figure 1B:
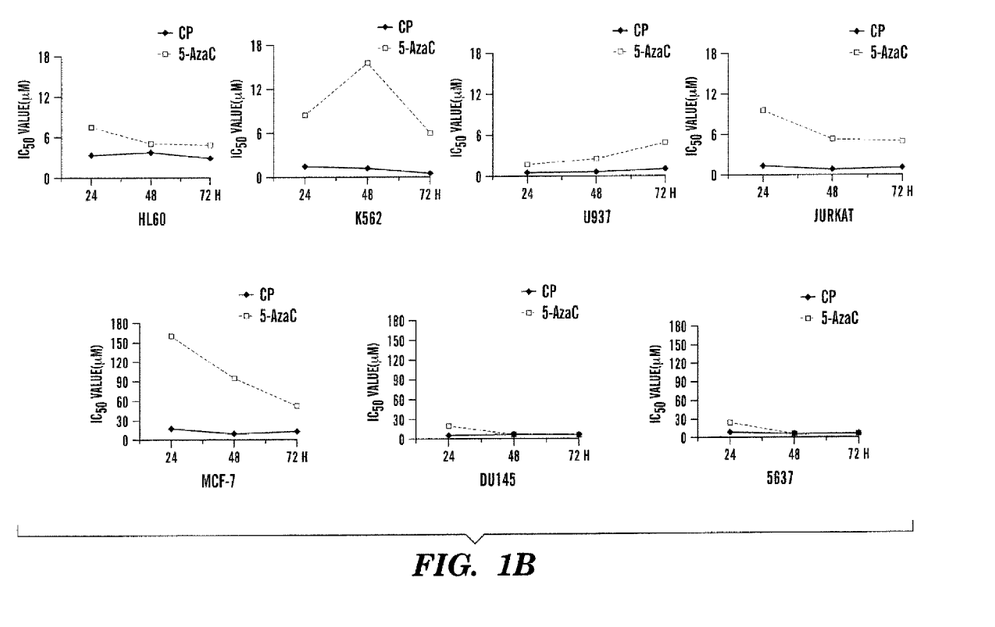

The cytotoxic activity of 5-azacytidine 5'-elaidate and 5-AzaC on leukemia and solid tumor cell lines was compared. Compared to 5-AzaC, the cytotoxic effect of 5-azacytidine 5'-elaidate was higher in all cell lines studied. Compared to solid tumors, leukemia cell lines were more sensitive to both 5-azacytidine 5'-elaidate (CP) and 5-AzaC See Table 2 (below) and FIGS. 1A-B.

TABLE 2

Table 2. Comparative cytotoxic activity of 5-azacytidine 5'-elaidate (CP) and 5-AzaC on leukemia and solid tumor cell lines. (IC50 values).

| | | 24 hour (μM) | 48 hour (μM) | 72 hour (μM) |
|---|---|---|---|---|
| U937 | CP | 0.44 | 0.60 | 0.87 |
| | 5-AzaC | 1.63 | 2.37 | 4.77 |
| K562 | CP | 1.26 | 0.92 | 0.42 |
| | 5-AzaC | 8.27 | 15.51 | 5.83 |
| HL60 | CP | 3.19 | 3.60 | 2.68 |
| | 5-AzaC | 7.28 | 4.92 | 4.71 |
| Jurkat | CP | 1.19 | 0.88 | 0.84 |
| | 5-AzaC | 9.5 | 5.32 | 4.77 |
| MCF-7 | CP | 19.10 | 9.32 | 9.99 |
| | 5-AzaC | >160 | 93.7 | 53.00 |
| DU145 | CP | 6.79 | 6.31 | 5.88 |
| | 5-AzaC | 20.94 | 7.11 | 7.20 |
| 5637 | CP | 9.39 | 5.95 | 3.52 |
| | 5-AzaC | 24.56 | 6.72 | 5.21 |

The cells were treated for 24, 48, and 72 hours and cytotoxicity was determined in the WST-1 assay. IC50 were calculated using CalcuSyn software.

The early onset of activity for 5-azacytidine 5'-elaidate, which is not observed in azacytidine, is a surprising result.

Example 8

Apoptosis Induction in Leukemia Cells

Figure 2A:
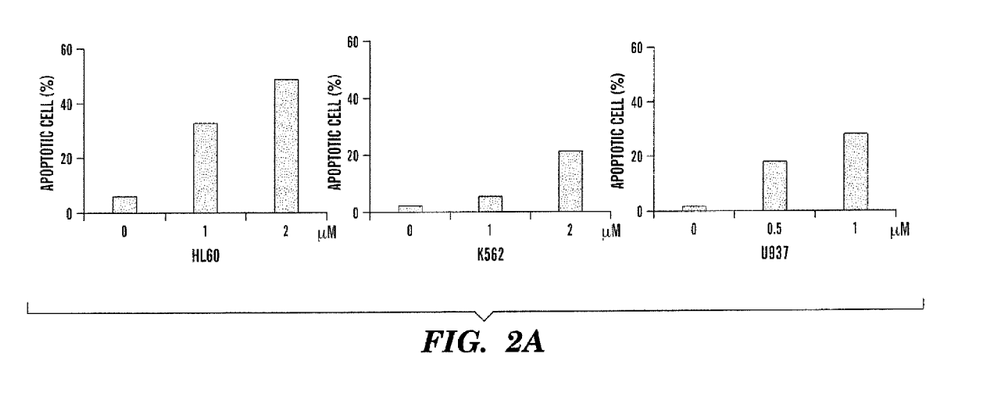
FIGS. 2A-B show graphs of apoptosis induction by 5-azacytidine 5'-elaidate in leukemia cells.
Figure 2B:
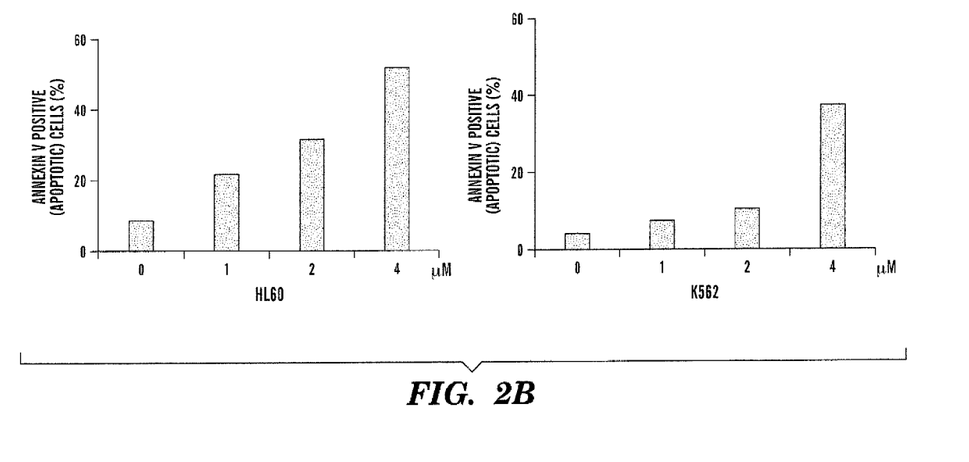

HL60, K562, and U937 cells were untreated or treated with 5-azacytidine 5'-elaidate (0.5-4 μM) for 24 hours. The percentage of apoptotic cells was determined with the aid of a fluoresence microscope after staining with acridine orange and ethidium bromide (See FIG. 2A). In the other set of experiments, HL60 and K562 were untreated or treated with 5-azacytidine 5'-elaidate (1, 2 or 4 μM) for 24 hours. The percentage of apoptotic cells was determined by flow cytometry using Annexin-V and PI staining. Both methods demonstrated that 5-azacytidine 5'-elaidate induced a concentration-dependent increase in the number of apoptotic cells. (See FIGS. 2a and 2b)

Example 9

Cell Cycle Progress

Figure 3:
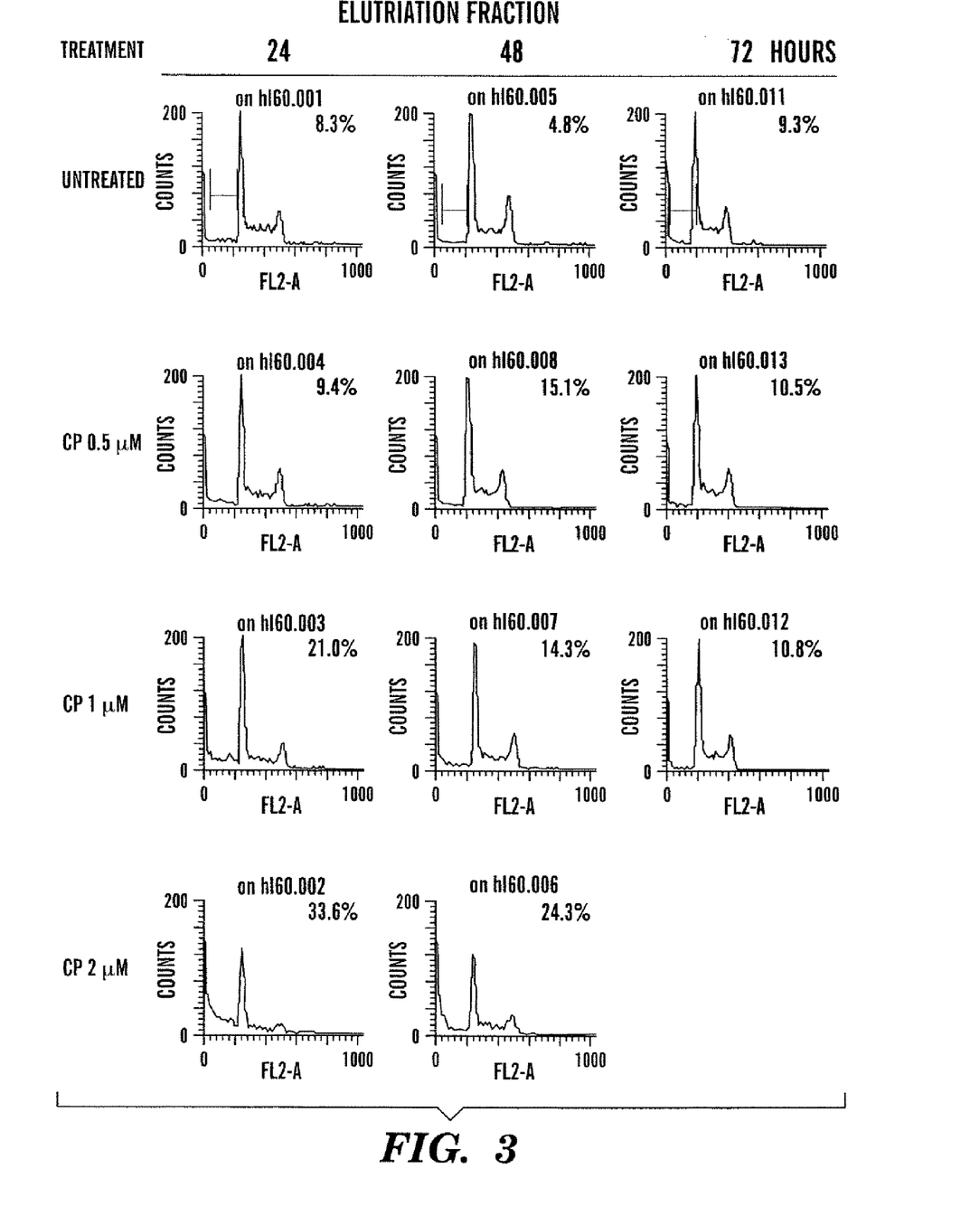
FIG. 3 shows graphs of the effect of 5-azacytidine 5'-elaidate (CP) exposure on cell cycle. Cells were cultured for the indicated lengths of time before being processed for analyses of DNA contents by flow cytometry. Numerical values in panel represent of gated cell population having sub-G1 DNA contents.

Effect of exposure to 5-azacytidine 5'-elaidate on cell cycle was studied. Cells were cultured for the indicated lengths of time before being processed for analyses of DNA contents by flow cytometry. Numerical values in a panel represent gated cell population with sub-G1 DNA contents. The most significant changes were observed after 24 hours of treatment. Compared to control (8.3%), the percentage in Sub-G1 phase (apoptotic cells) was increased up to 33.6% in the cells treated with 5-azacytidine 5'-elaidate 2 μM, and in G1, S, and G2/M phase were decreased. Results are summarized in FIG. 3 and Table 3, below. These results confirmed the apoptosis induction by 5-azacytidine 5'-elaidate and demonstrated that 5-azacytidine 5'-elaidate affected the cell cycle at concentration-dependent manner.

TABLE 3

Table 3. Effect of 5-azacytidine 5'-elaidate (CP) exposure on cell cycle. % cell

| | | dose (μM) | Sub G1 | G1 | S | G2/M |
|---|---|---|---|---|---|---|
| 24 hour | | | | | | |
| 1 | control | 0 | 8.26 | 38.61 | 33.35 | 12.7 |
| 2 | cp | 0.5 | 9.41 | 43.66 | 28.15 | 11.05 |
| 3 | | 1 | 21.02 | 36.17 | 18.98 | 8.82 |
| 4 | | 2 | 33.59 | 23.45 | 9.14 | 2.64 |
| 48 hour | | | | | | |
| 1 | control | 0 | 4.8 | 41.1 | 31.14 | 18.34 |
| 2 | cp | 0.5 | 15.14 | 34.79 | 42.96 | 2.53 |
| 3 | | 1 | 14.34 | 28.07 | 30.06 | 17.91 |
| 4 | | 2 | 24.34 | 22.51 | 15.62 | 7.78 |

TABLE 3-continued

Table 3. Effect of 5-azacytidine 5'-elaidate (CP) exposure on cell cycle. % cell

| | | dose (μM) | Sub G1 | G1 | S | G2/M |
|---|---|---|---|---|---|---|
| 72 hour | | | | | | |
| 1 | control | 0 | 9.28 | 47.72 | 27.39 | 14.64 |
| 2 | cp | 0.25 | 10.88 | 40.14 | 28.13 | 18.25 |
| 3 | | 0.5 | 10.54 | 38.72 | 29.18 | 18.82 |
| 4 | | 1 | 10.75 | 40.67 | 28.77 | 18.26 |

Cells were cultured for the indicated lengths of time before being processed for analyses of DNA contents by flow cytometry. The number shown is the cell percentage in various phases.

Example 10

Differentiating Induction

Figure 4A:
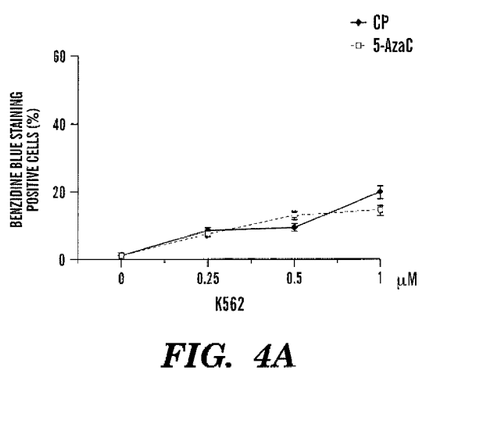
FIGS. 4A-B shows graphs of the differentiating inducing effects of 5-azacytidine 5'-elaidate and 5-AzaC. K562 and U937 were exposed to 5-azacytidine 5'-elaidate (CP) or 5-AzaC (0.125-1 µM) for 14 days. After initial treatment on day 0, cells were exposed to the new portions of drugs on day 4, day 7, and day 10. The differentiation was evaluated by NBT (U937) (FIG. 4A) or benzidine staining (K562) (FIG. 4B).
Figure 4B:
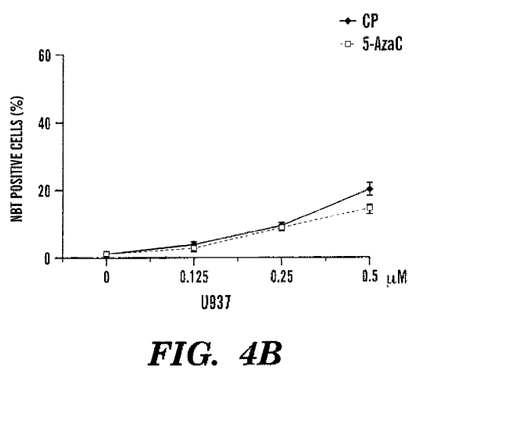

Cell differentiation was studied in terms of morphology. Since single exposure (96 hours) had no effect, cells were exposed to 5-azacytidine 5'-elaidate or 5-AzaC for 11 (HL60 cells) or 14 (U937 and K562 cells) days. After initial treatment on day 0, cells were exposed to the new portions of drugs on day 4, 7, and 10. The differentiation was evaluated by NBT reduction assay (U937 and HL60) or by benzidine staining (K562). Although 5-azacytidine 5'-elaidate was slightly more effective, both agents did not induce significant differentiation. See FIGS. 4A-B.

Example 11

Metabolic Stability of 5-Aza-5'-Elaidic Acid Ester in Pooled Human Plasma

5-Aza-C-5'-elaidic acid ester was spiked into pooled human plasma at five concentration levels (0.1, 1, 3, 10, and 30 μM, respectively). The mixture was incubated in a shaking water batch at 37° C. Aliquots (100 μl) of the incubation solutions were withdrawn in triplicate (n=3) at the designed incubation period (0, 15, 30, 60 and 120 minutes), and plasma protein was immediately precipitated using acetonitrile containing 0.1% formic acid (300 μl). Negative controls were prepared with the test compound and Aza-C in the assay buffer (PBS, pH 7.4) at one concentration of incubation (1 μM). After centrifugation, the supernatant was directly introduced for LC-MS-MS analysis. See Table 4.

TABLE 4

Metabolic stability of 5-Aza-5'-elaidic acid ester in pooled human plasma

| Concentration | % Remaining of initial (mean ± SD, n = 3) | | | | | Half-Life |
|---|---|---|---|---|---|---|
| (μM) | 0 min | 15 min | 30 min | 60 min | 120 min | (min) |
| 0.1 | 100 | 95.8 ± 3.0 | 95.0 ± 2.0 | 92.1 ± 3.4 | 59.0 ± 1.6 | 161 |
| 1 | 100 | 93.3 ± 1.1 | 88.9 ± 1.1 | 79.8 ± 2.6 | 52.5 ± 3.1 | 130 |
| 3 | 100 | 99.0 ± 3.5 | 96.0 ± 3.0 | 85.4 ± 3.4 | 56.6 ± 1.6 | 141 |
| 10 | 100 | 96.0 ± 2.0 | 93.1 ± 0.0 | 77.1 ± 3.1 | 39.1 ± 1.7 | 86 |
| 30 | 100 | 97.7 ± 3.5 | 90.4 ± 2.6 | 78.5 ± 1.7 | 47.4 ± 1.1 | 109 |

Example 12

Cytotoxicity of Aza-C and 5-Aza-C-5'-Elaidic Acid

The cytotoxicity of Aza-C and 5-Aza-C-5'-elaidic acid was determined in a breast cancer cell line MT-3 and the adriablastin resistant cell line MT-3/ADR. The MT-3/ADR overexpress the MDR-1/p-glycoprotein. The cells were seeded in 96-well plates with $5 \times 10^3$ cells per well, in RPMI 1640 medium with 2 mM glutamine and 10% FBS. The cells were incubated for 24 hours. The test compounds were dissolved in DMSO and further diluted in medium just prior to use. Six wells were used per test concentration. The cells were incubated with test compound for 24 hours. 20 µl of freshly prepared MTT solution was added to each well and incubated for 4 hours. IC50 values were determined from growth curves presented graphically based on 8 different concentrations ranging from 0.01 µM to 100 µM. The results are presented in Table 5. Similar activity was obtained for Aza-C and 5-Aza-C-5'-elaidic acid in the MT-3 breast carcinoma cell line, but in the MT-3/ADR resistant cell line the activity of Aza-C was lost. No activity was observed in the concentration range tested up to 100 µM, whilst 5-Aza-C-5'-elaidic acid was active with a similar IC50 value in the resistant cell line and the non-resistant MT-3 line. This may be of importance in the treatment of resistant cancer. See Table 5.

TABLE 5

Cytotoxic activity of and 5-Aza-C-5'-elaidic acid in the breast carcinoma cell line MT-3 with or without multi drug resistance.

| | Aza-C IC50 (µM) | 5-Aza-C-5'-elaidic acid IC50(µM) |
|---|---|---|
| MT-3 breast carcinoma | 12.62 ± 2.35 | 17.03 ± 15.75 |
| MT-3/ADR resistant breast carcinoma | >100 | 14.82 ± 12.76 |

Example 13

Impact of Nucleoside Transporter Inhibition Aza-C and 5-Aza-C-5'-Elaidic Acid The impact of nucleoside transporter inhibition on cytotoxic activity has been evaluated in Hela mutant cervix carcinoma cells for Aza-C and 5-Aza-C-5'-elaidic acid. Dipyridamole was used as an inhibitor of the equilibrative nucleoside transporters hENT1 and hENT2. The cells were seeded in 96-well plates with $5 \times 10^3$ cells per well, in RPMI 1640 medium with 2 mM glutamine and 10% FBS. The cells were pre-incubated for 24 hours. Dipyridamole (10 µM) was added to the cells 30 minutes prior to the addition of the test compounds. The test compounds were dissolved in DMSO and further diluted in medium just prior to use. Six wells were used per test concentration. The cells were incubated with test compound for 72 hours. 20 µl of freshly prepared MTT solution was added to each well and incubated for 4 hours. IC50 values were determined from growth curves presented graphically based on 8 different concentrations ranging from 0.01 µM to 100 µM. The results are presented in Table 6. The activity of Aza-C was reduced 3 fold by the addition of the nucleoside transport inhibitor dipyridamole, indicating that the influx and efflux of Aza-C are partly dependent on the nucleoside transporters hENT1 and hENT2. The cytotoxic activity of 5-Aza-C-5'-elaidic acid was not only maintained but increased 50-fold when the hENT1 and hENT2 nucleoside transporters were blocked by the use of dipyridamole. The increased activity in cells where the nucleoside transporters are blocked by dipyridamole is surprising, and may indicate even higher activity in patients with resistance to treatment caused by lack of nucleoside transporters. See Table 6.

TABLE 6

Cytotoxic activity of Aza-C and 5-Aza-C-5'-elaidic acid in Hela cervix carcinoma cells with or without addition of nucleoside transport inhibitor.

| | Azacytidine IC50 (µM) | 5-Aza-C-5'-elaidic acid IC50 (µM) |
|---|---|---|
| Hela | 4.32 | 12.00 |
| Hela with dipyridamole | 12.77 | 0.23 |

Example 14

Activation of the Nuclear Transcription Factor-κB (NFκB)

The activation of the nuclear transcription factor-κB (NFκB) was evaluated in order to estimate the impact on inflammation. NFκB is involved in the control of a large number of both immune and inflammatory responses, developmental processes, cellular growth and apoptosis.

Figure 5:
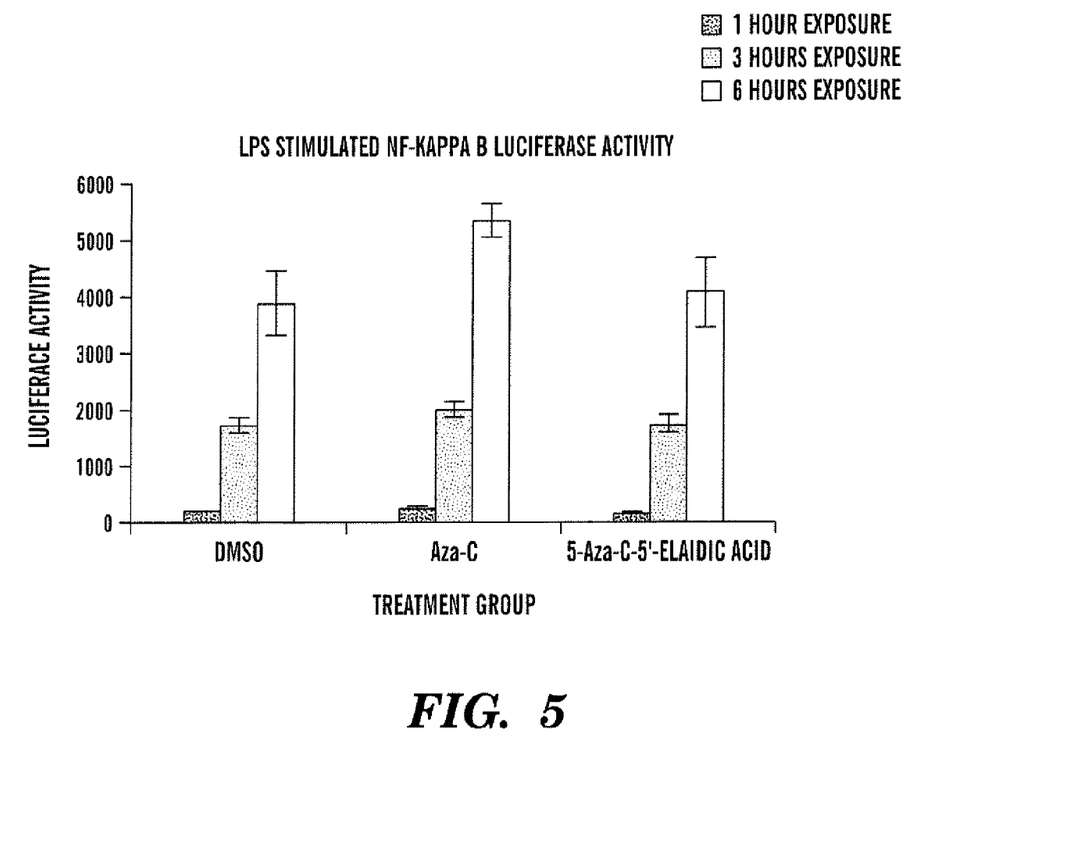
FIG. 5 is a graph showing lipopolysaccharide (LPS) stimulated NFκB luciferase activity measured in U937 cells, exposed to Aza-C or 5'-Aza-C-5'-elaidic acid ester.

NFκB-luciferase reporter genes were used to determine the influence of Aza-C and 5-Aza-C-5'-elaidic acid on NFκB-induced luciferase activity in a human monocytic cell line U937, stably transfected with a luciferase reporter containing three NFκB-binding sites. The induction of NFκB was performed using lipopolysaccharide (LPS) at 1 µg/ml for 30 minutes prior to the addition of Aza-C or 5-Aza-C-5'-elaidic acid in the concentrations 10 nM to the medium. The cells were cultured in RPMI-1640 medium including 10% fetal bovine serum. Before stimulation with LPS the cells were transferred to medium containing only 2% fetal bovine serum. Luciferase activity was measured by imaging in an IVIS imaging System 100 (Xenogen Corp., USA) after 1, 3 or 6 hours. The LPS stimulation increased with time over the 6 hours followed in the DMSO treated control cells. Exposure to 10 nM Aza-C further increased the LPS induced NFκB activation compared to the DMSO treated control. 5-azacytidine-5'-eladiate did not differ from the DMSO control in LPS stimulated NFκB activity. Generally, a positive stimulation of NFκB as observed for azacytidine is not positive, and it is positive that the LPS stimulation is not further increased by 5'Aza-C-5'-elaidic acid. See FIG. 5.

Example 15

Gene Expression of Estrogen Receptor β (ERβ) in Breast Cancer Cell Lines After Treatment with Azacytidine or 5-Azacytidine 5'-elaidate The gene expression (determined on RNA level) of estrogen receptor beta was determined by quantitative real-time PCR. (TaqMan). MCF-7 mammary carcinoma cells were grown in estrogen deficient media (Phenol-Red-free RPMI with 2% glutamine and 10% charcoal-dextran treated fetal calf serum). The cells were seeded into 25 cm² flasks and attached for 24 hours prior to treatment with 1 µM of azacytidine or 5-azacytidine 5'-elaidate. One untreated control was included as control. The cells were harvested after 5 days of exposure to the compounds; they were harvested by trypsination, washed and shock frozen in liquid nitrogen.

The total RNA was extracted from approximately $10^6$ shock frozen MCF-7 cells. The RNA concentration and purity was measured, and RNA was transcribed into cDNA using TaqMan Reverse Trancription reagents (N808-0234). Real-time quantification was performed using standard protocols and premixed PCR reagents. The primer-probe mixes were ordered from Applied Biosystems, ER β (ID Hs00230957_m1) and housekeeping gene hydrocylmethylbilane synthase HMBS (ID Hs00609297_m1). Gene expression was calculated using the comparative delta-delta $C_t$ method. The induction of expression of ER β was 5.26 fold after exposure to 5-azacytidine 5'-elaidate compared to only 2.51 fold after exposure to azacytidine. See Table 7. This may be of high relevance in hormone refractory tumors where hormone sensitivity can be restored. See Table 7.

TABLE 7

|  | Ct ER β | Ct HMBS | delta | Delta delta | x-fold induction of the ERβ gene |
|---|---|---|---|---|---|
| Untreated | 35.36 | 25.91 | 9.45 |  |  |
| 1 μM 5'Aza-C-5'-elaidic acid | 32.97 | 25.92 | 7.06 | −2.40 | 5.26 |
| 1 μM aza-C | 34.31 | 26.18 | 8.13 | −1.32 | 2.51 |

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound according to Formula (I)

(I)

wherein,
R is $R_5C(O)$;
$R_1$ is where the crossing dashed line illustrates the bond formed joining $R_1$ to the molecule of Formula (I);
$R_2$ is H and $R_3$ is OH;
$R_4$ is H; and
$R_5$ is $CH_3$—$(CH_2)_7$—CH═CH—$(CH_2)_7$—,
or a pharmaceutical salt thereof.

2. A pharmaceutical composition comprising:
the compound of claim 1 and
a pharmaceutical excipient, diluent, and/or carrier.

3. A method of treating a subject for a neoplastic condition, said method comprising:
selecting a subject with a neoplastic condition and administering to the subject a compound of the formula:

(I)

wherein,
R is H;
$R_1$ is where the crossing dashed line illustrates the bond formed joining $R_1$ to the molecule of Formula (I);
$R_2$ is H and $R_3$ is OH;
$R_4$ is H; and
$R_5$ is $CH_3$—$(CH_2)_7$—CH═CH—$(CH_2)_7$—,
or a pharmaceutical salt thereof, under conditions effective to treat the neoplastic condition in the subject.

4. The method of claim 3, wherein the neoplastic condition is a cancerous disease.

5. The method of claim 4, wherein the cancerous disease is a solid tumor or a hematological cancer or malignancy.

6. The method of claim 4, wherein the cancerous disease is leukemia, lymphoma, multiple myeloma, or myelodysplastic syndrome.

7. The method of claim 5, wherein the solid tumor is a cancer of a tissue selected from the group consisting of breast, ovary, prostate, brain, bladder, and lung.

8. A method of treating a subject for an inflammatory condition, said method comprising:
selecting a subject with an inflammatory condition and administering to the subject a compound of the formula:

(I)

wherein,
R is H;

$R_1$ is where the crossing dashed line illustrates the bond formed joining $R_1$ to the molecule of Formula (I);
$R_2$ is H and $R_3$ is OH;
$R_4$ is H; and
$R_5$ is $CH_3\text{—}(CH_2)_7\text{—}CH\text{=}CH\text{—}(CH_2)_7\text{—}$,
or a pharmaceutical salt thereof, under conditions effective to treat the inflammatory condition in the subject.

9. The method of claim 8, wherein the inflammatory condition is an inflammatory state of the lung, connective tissue, gastro-intestinal tract, or vasculature.

* * * * *